United States Patent
Chmielewski

[19]

[11] Patent Number: 6,068,620
[45] Date of Patent: May 30, 2000

[54] ABSORBENT LAMINATE

[75] Inventor: Harry J. Chmielewski, Norcross, Ga.

[73] Assignee: Paragon Trade Brands, Norcross, Ga.

[21] Appl. No.: 09/050,003

[22] Filed: Mar. 30, 1998

[51] Int. Cl.[7] ...................................................... A61F 13/15
[52] U.S. Cl. ........................ 604/378; 604/358; 604/367; 604/368; 604/374; 604/385.1; 604/369; 604/370; 604/371; 604/372; 604/373; 604/375
[58] Field of Search ..................................... 604/368, 359, 604/385.1, 385.2, 358, 367, 374, 369, 370, 371, 372, 373, 375, 378

[56] References Cited

U.S. PATENT DOCUMENTS

| | | |
|---|---|---|
| 5,021,050 | 6/1991 | Iskra . |
| 5,281,207 | 1/1994 | Chmielewski et al. . |
| 5,318,553 | 6/1994 | Weeks et al. . |
| 5,350,370 | 9/1994 | Jackson et al. . |
| 5,356,403 | 10/1994 | Faulks et al. . |
| 5,411,497 | 5/1995 | Tanzer et al. . |
| 5,429,628 | 7/1995 | Trinh et al. . |
| 5,447,977 | 9/1995 | Hansen et al. . |
| 5,494,622 | 2/1996 | Heath et al. . |
| 5,520,673 | 5/1996 | Yarbrough et al. . |
| 5,558,655 | 9/1996 | Jezzi et al. . |
| 5,562,645 | 10/1996 | Tanzer et al. . |
| 5,571,618 | 11/1996 | Hansen et al. . |
| 5,582,606 | 12/1996 | Bruemmer et al. . |
| 5,593,399 | 1/1997 | Tanzer et al. . |
| 5,609,727 | 3/1997 | Hansen et al. . |
| 5,611,879 | 3/1997 | Morman . |
| 5,611,885 | 3/1997 | Hansen et al. . |
| 5,651,862 | 7/1997 | Anderson et al. . |
| 5,728,084 | 3/1998 | Palumbo et al. . |

FOREIGN PATENT DOCUMENTS

| | | |
|---|---|---|
| 9711659 | 3/1997 | WIPO . |

*Primary Examiner*—John G. Weiss
*Assistant Examiner*—Miley Craig Peppers
*Attorney, Agent, or Firm*—Hunton & Williams

[57] ABSTRACT

A disposable absorbent garment comprising a topsheet, a backsheet and an absorbent core disposed between the topsheet and backsheet is disclosed. The absorbent core is formed from at least one and preferably more than one laminate comprising three layers, including an upper layer, a lower layer and a central fibrous layer containing from about 50–95% by weight superabsorbent polymer. The upper and lower layers comprise tissue, airlaid fluff pulp or synthetic non-woven fibrous layers. The upper and lower layers together assist to maintain the integrity of the core during manufacture and in use, contain the superabsorbent polymer within the insult area of the garment and act to diffuse multiple insults so that gel blocking is minimized. The absorbent garment thus formed is very thin, lightweight and economical.

32 Claims, 5 Drawing Sheets

ABSORBENT LAMINATE

FIELD OF THE INVENTION

The present invention relates generally to an absorbent core for a disposable absorbent garment, and more particularly to an absorbent core comprising one or more laminates in which one of the layers of the laminate or laminates contains from about 50–95% by weight particulate or fibrous superabsorbent polymer (SAP).

BACKGROUND OF THE INVENTION

Traditionally, disposable absorbent garments such as infant diapers or training pants, adult incontinence products and other such products are constructed with a moisture-impervious outer backing sheet, a moisture-pervious body-contacting inner liner sheet, and a moisture-absorbent core sandwiched between the liner and backing sheets.

Much effort has been expended to find cost-effective materials for absorbent cores which display good liquid absorbency and retention. Superabsorbent materials in the form of granules, beads, fibers, bits of film, globules, etc., have been favored for such purposes. Such superabsorbent materials are generally polymeric gelling materials which are capable of absorbing and retaining even under moderate pressure large quantities of liquid, such as water and body wastes, relative to their weight.

The superabsorbent material is generally a water-insoluble but water-swellable polymeric substance capable of absorbing water in an amount which is at least ten times the weight of the substance in its dry form. In one type of superabsorbent material, the particles or fibers may be described chemically as having a back bone of natural or synthetic polymers with hydrophilic groups or polymers containing hydrophilic groups being chemically bonded to the back bone or an intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

The ability of a superabsorbent material to absorb liquid is dependent upon the form, position and/or manner in which particles of the superabsorbent are incorporated into the absorbent core. Whenever a particle of the superabsorbent material and absorbent core is wetted, it swells and forms a gel. Gel formation can block liquid transmission into the interior of the absorbent core, a phenomenon called "gel blocking." Gel blocking prevents liquid from rapidly diffusing or wicking past the "blocking" particles of superabsorbent, causing portions of a partially hydrated core to become inaccessible to multiple doses of urine. Further absorption of liquid by the absorbent core must then take place via a diffusion process. This is typically much slower than the rate at which liquid is applied to the core. Gel blocking often leads to leakage from the absorbent article well before all of the absorbent material in the core is fully saturated.

Despite the incidence of gel blocking, superabsorbent materials are commonly incorporated into absorbent cores because they absorb and retain large quantities of liquid, even under load. However, in order for superabsorbent materials to function, the liquid being absorbed in the absorbent structure must be transported to unsaturated superabsorbent material. In other words, the superabsorbent material must be placed in a position to be contacted by liquid. Furthermore, as the superabsorbent material absorbs the liquid it must be allowed to swell. If the superabsorbent material is prevented from swelling, it will cease absorbing liquids.

Adequate absorbency of liquid by the absorbent core at the point of initial liquid contact and rapid distribution of liquid away from this point is necessary to ensure that the absorbent core has sufficient capacity to absorb subsequently deposited liquids. Prior art absorbent cores have thus attempted to absorb quickly and distribute large quantities of liquids throughout the absorbent core while minimizing gel blocking during absorption of multiple doses of liquid.

In general, some of the most important performance attributes of an absorbent core of a diaper (or any other absorbent garment) are functional capacity, rate of absorption, and core stability in use. Absorption under load or AUL is a good measure of functional capacity and the rate at which that absorption occurs. AUL is a function of both SAP basis weight (mass per unit area) and composition of SAP used in the composite. Baby diaper cores that contain only fluff pulp and a high gel strength SAP maintain adequate SAP efficiency if the core contains less than about 50% SAP. Fluff/SAP diaper cores containing more than 50% SAP result in lower SAP efficiency because of gel blocking. Although fluff/SAP cores at greater than 50% SAP can provide adequate absorbency, the overall basis weight of the core must be increased to compensate for the lower efficiency of the SAP. Increasing the basis weight decreases the performance/cost ratio of the absorbent core, making them uneconomical. Also, increased basis weights tend to affect the fit and comfort of the garment, as well as impacting the packaging and shipping costs.

These are just a few of the disadvantages of the prior art which the preferred embodiments seek to address.

SUMMARY OF THE INVENTION

It is an object of the invention to provide an absorbent garment having an improved ability to retain fluids.

It is a further object of the invention to provide an absorbent garment with an absorbent core having SAP particles as a substantial percentage of its basis weight, but at the same time reducing gel blocking, i.e., retaining high SAP efficiency.

It is still yet a further object of the invention to provide an absorbent garment with an absorbent core having high dry and wet strength for processing and in-use performance.

It is yet a further object of the invention to provide an absorbent core comprising one or more laminates wherein one of the layers of the laminate or laminates is a high-density, SAP-containing layer.

It is still yet a further object of the invention to provide a thin, dense absorbent laminate which may be combined with other such thin, dense absorbent laminates to form an absorbent core.

These and other objects of the invention are achieved by a disposable absorbent article comprising a top sheet, at least a portion of which is liquid pervious, a substantially liquid impervious back sheet and an absorbent core disposed between the top sheet and the back sheet. The absorbent article has a front waist region, a rear waist region and a crotch region positioned between the front and rear waist regions. Leg elastics are provided along the leg openings for securely holding the leg openings against the thighs of the wearer to improve containment and fit. A fastening system, either resealable or permanent, holds the absorbent article around the wearer's waist. A pair of stand-up leg gathers or waist containment flaps may be attached to or formed from the body's side surface of the top sheet.

The preferred embodiments of the absorbent garment each include an absorbent core comprising one or more laminated layers. Each laminate is formed from one or more layers, and preferably three layers. The laminate preferably comprises three layers, a high efficiency, SAP-containing layer sandwiched between tissue layers. Other non-SAP-containing roll good materials such as latex or thermally bonded airlaid fluff pulp, (e.g., roll good available from Walkisoft, Merfin or Fort James), or synthetic spunbonded, carded, or hydro-entangled non-woven may be positioned above and below the absorbent core. At least one of the laminates in the absorbent core preferably contains 50–95% by weight particulate or fibrous SAP and at least one other fibrous or particulate material that is capable of maintaining high SAP efficiency. SAP efficiency can be expressed as the ratio of the actual SAP absorbency under load, or AUL (expressed as grams of saline absorbed per gram of SAP in the laminate), and the maximum SAP AUL obtained under ideal conditions of low basis weight where gel blocking does not occur. SAP concentrations of 50–95% provide thinner roll good composites for efficient shaping and handling. High SAP concentrations also provide thinner absorbent cores which provide new options for product design. The laminates can be made using either a wet or dry process.

Most preferably, the absorbent garment of the preferred embodiments includes an absorbent core comprising two laminates. Each of the two laminates are similar in design and preferably comprise outer tissue layers between which is sandwiched 50–95% by weight particulate or fibrous SAP, with the balance comprising at least one other fibrous or particulate material. The end edges of the laminates are generally exposed. Since the laminates each contain a relatively high concentration of SAP, provision is made to contain the SAP within the absorbent core proper.

In one preferred embodiment, one of the laminates is wrapped along its longitudinal length by another C-folded laminate, with the C-folded laminate attached to the backsheet. In an alternative embodiment, one laminate sits atop another laminate. A tissue layer is positioned above the upper laminate and extends beyond the exposed side edges of the laminate. The tissue layer is attached to the backsheet at opposite lateral sides of the laminates for SAP containment.

Forming the absorbent core with one or more laminates "decouples" key performance attributes of traditional absorbent cores. In general, the various layers of an absorbent core are designed with competing interests. A compromise is usually made at the sacrifice of the optimal performance attributes of each of the individual layers. By "decoupling" the performance attributes of the individual layers, the absorbent core of the preferred embodiments optimizes the key characteristic performance attributes of each of the laminates resulting in overall improved performance over prior art absorbent cores. More particularly, outer layers of absorbent cores are generally designed for optimal wet/dry strength, liquid acquisition and distribution, and SAP containment. The inner layers of absorbent cores are generally designed for optimal absorbency and SAP efficiency. Designers of absorbent cores in the past have had to combine the attributes of the outer and inner layers into a homogeneous composite, often leading to an unacceptable compromise.

The absorbent core of the preferred embodiments, by having one or more laminates with high density SAP in the central or middle layer thereof, allows the absorbent core to be designed without compromising performance attributes of the individual components. For example, significant SAP efficiency improvement is realized when one or more laminated layers is employed. Specifically, the absorbent cores of the preferred embodiment realize about 27 g/g SAP or about 27/30=90% SAP efficiency. The prior art, in comparison, realizes equal to or less than about 70% SAP efficiency for SAP/pulp in a homogenous core that is equal to or greater than 80% SAP and 20% fluff pulp.

In addition to the foregoing advantages, the absorbent garment having an absorbent core comprising one or more highly concentrated SAP laminates improves the comfort and fit of the garment. Further, due to the thinness of the resulting product, less packaging material is needed for the same amount of product, and shipping and handling costs are lowered.

These and other objects, features and advantages of the preferred embodiments will become more readily apparent when the detailed description of the preferred embodiments is read in conjunction with the attached drawings.

DETAILED DESCRIPTION OF THE PREFERRED EMBODIMENTS

As used herein, the term "absorbent garment" refers to garments that absorb and contain exudates, and more specifically, refers to garments which are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term "disposable absorbent garment" refers to absorbent garments that are intended to be discarded or partially discarded after a single use (i.e., they are not intended to be laundered or otherwise restored or reused). The term "unitary disposable absorbent garment" refers to a disposable absorbent garment that is essentially a single structure (i.e., it does not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above. Preferably, the absorbent core is thin in order to improve the comfort and appearance of a garment. The importance of thin, comfortable garments is disclosed, for example, in U.S. Pat. No. 5,098,423 to Pieniak et al., which is herein incorporated by reference.

Figure 1:
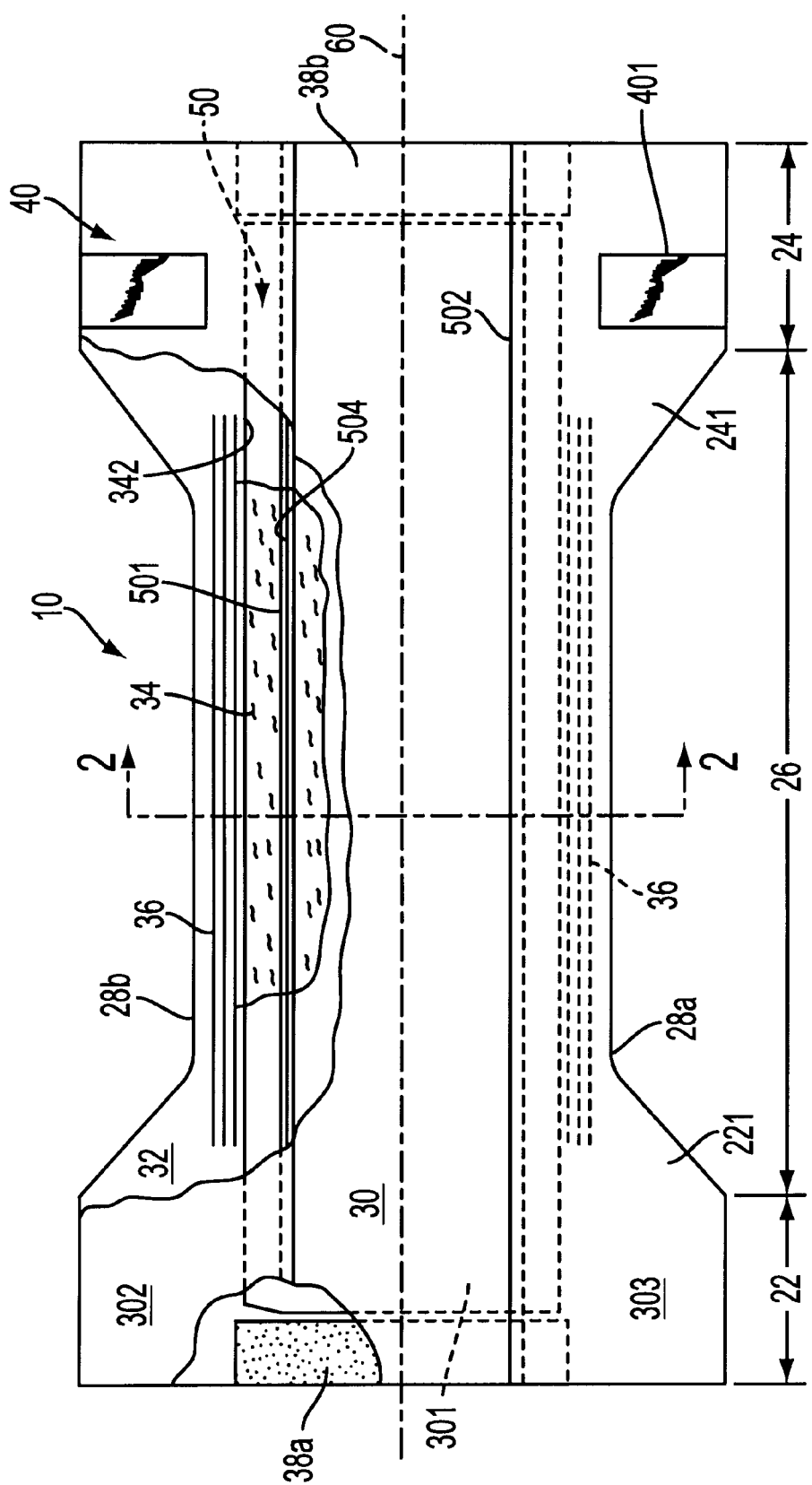
FIG. 1 is plan view of an absorbent garment incorporating the fiber laminate absorbent core with the effects of the elastics of the garment removed.

A preferred embodiment of the present invention comprises a disposable absorbent garment 10 such as shown, for example, in FIG. 1. Again, it should be understood, however, that the present invention is applicable to other types of absorbent garments. For simplicity, the invention will be described in terms of a diaper. With reference to FIG. 1, the diaper 10 according to a first preferred embodiment is shown in a relaxed condition with the effects of the elastics removed for purposes of clarity in description. The diaper 10 has a generally hourglass shape and can generally be defined in terms of a front waist region 22, a back waist region 24, and a crotch region 26. Alternatively, the diaper can be configured in a generally rectangular shape or in a "T" shape. A pair of leg openings 28a, 28b extend along at least a portion of the crotch region 26. The diaper preferably comprises a top sheet 30, a back sheet 32, which may be substantially co-terminous with the top sheet 30, and an absorbent core laminate 34 disposed between at least a portion of the top sheet 30 and back sheet 32. One or more pairs of leg elastics 36 (three pairs are shown in FIG. 1) extend adjacent to leg openings 28a, 28b, respectively.

Figure 2:
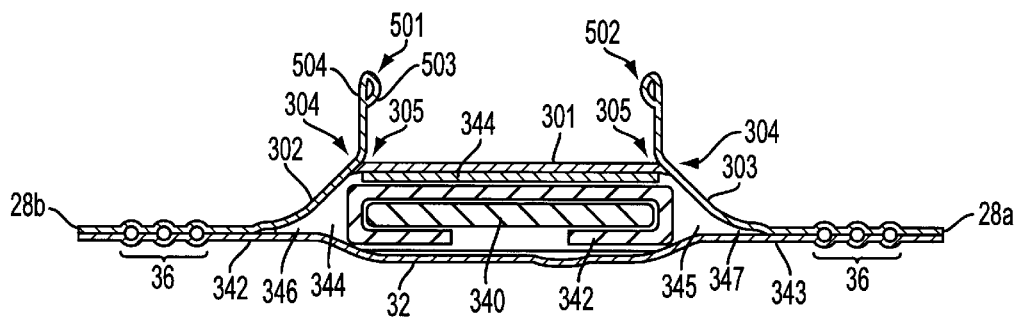
FIG. 2 is cross-section of the absorbent garment taken along line 2—2 of FIG. 1 illustrating one embodiment for the fiber laminate absorbent core.

The diaper may further include a front waist elastic system 38a, a back waist elastic system 38b, a fastening system 40 (e.g., tape or other suitable mechanical fastener) and a waste containment system 50 in the form of waste containment flaps 501, 502. Waste containment flaps 501, 502 (FIG. 2) preferably extend from the front waist region 22 to the back waist region 24 along opposite sides of a longitudinal center line or axial center line 60 of the diaper 10, or alternatively only along a portion thereof. The front waist region 22 and rear waist region 24 include ear portions 221, 241 extending outwardly from the leg openings 28a, 28b.

Due to the wide variety of backing and liner sheet construction and materials currently available, the invention is not intended to be limited to any specific materials or constructions of these components. The back sheet 32 is of any suitable pliable liquid-impervious material known in the art. Typical back sheet materials include films of polyethylene, polypropylene, polyester, nylon, and polyvinyl chloride and blends of these materials. For example, the back sheet can be of a pigmented polyethylene film having a thickness in the range of 0.02–0.04 mm. The moisture-pervious top sheet 30 can be of any suitable relatively liquid-pervious material known in the art that permits passage of liquid therethrough. Non-woven liner sheet materials are exemplary because such materials readily allow the passage of liquids to the underlying absorbent core 34. Examples of suitable liner sheet materials include non-woven spunbond or carded webs of polypropylene, polyethylene, nylon, polyester and blends of these materials.

The backsheet 32 and the topsheet 30 are "associated" with one another. The term "associated" encompasses configurations whereby the topsheet 30 is directly joined to the backsheet 32 by affixing the topsheet 30 directly to the backsheet 32, and configurations whereby the topsheet 30 is indirectly joined to the backsheet 32 by affixing the topsheet 30 through intermediate members which in turn are affixed to the backsheet 32. While the backsheet 32 and topsheet 30 in the preferred embodiment have substantially the same dimensions, they may also have different dimensions.

In addition, the backsheet 32 may be covered with a fibrous, nonwoven fabric such as is disclosed for example in U.S. Pat. No. 4,646,362, which is hereby incorporated by reference. Materials for such a fibrous outer liner include a spun-bonded nonwoven web of synthetic fibers such as polypropylene, polyethylene or polyester fibers; a nonwoven web of cellulostic fibers, textile fibers such as rayon fibers, cotton and the like, or a blend of cellulostic and textile fibers; a spun-bonded nonwoven web of synthetic fibers such as polypropylene; polyethylene or polyester fibers mixed with cellulostic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulostic, pulp or textile fibers. Alternatively, the backsheet may comprise three panels wherein a central poly backsheet panel is positioned adjacent the absorbent core while outboard non-woven breathable side backsheet panels are attached to the side edges of the central poly backsheet panel. Alternatively, the backsheet may be formed from microporous poly coverstock for added breathability.

Alternatively, the top sheet may be formed of three separate portions or panels. The first top sheet panel 301 may comprise a central top sheet panel formed from preferably a liquid-pervious material that is either hydrophobic or hydrophilic. The central top sheet panel 301 may be made from any number of materials, including synthetic fibers (e.g., polypropylene or polyester fibers), natural fibers (e.g., wood or cellulose), apertured plastic films, reticulated foams and porous foams to name a few. One preferred material for a central top sheet panel 301 is a cover stock of single ply non-woven material which may be made of carded fibers, either adhesively or thermally bonded, perforated plastic film, spunbonded fibers, or water entangled fibers, which generally weigh from 0.3–0.7 oz./sq. yd. and have appropriate and effective machine direction and cross-machine direction strength suitable for use as a baby diaper cover stock material. The central top sheet 301 panel preferably extends from substantially the front waist region 22 to the back waist region 24 or a portion thereof.

The second and third top sheet panels 302, 303 in this alternative embodiment may be positioned laterally outside of the central top sheet panel 301. The outer top sheet panels 302, 303 are preferably substantially liquid-impervious and hydrophobic, preferably at least in the crotch area. The outer edges of the outer top sheet panels may substantially follow the corresponding outer perimeter of the back sheet 32. The material for the outer top sheet portions or panels is preferably polypropylene and can be woven, non-woven, spunbonded, carded or the like, depending on the application.

The inner edges 304 (FIG. 2) of the outer topsheet portions or panels 302, 303 preferably are attached by, e.g., an adhesive, to the outer edges 305 of the inner topsheet portion or panel 301. At the point of connection with the outer edges 305 of the inner topsheet portion or panel 301, the inner edges 304 of the outer topsheet portions or panels 302, 303 extend upwardly to form waste containment flaps 501, 502. The waste containment flaps 501, 502 are preferably formed of the same material as the outer topsheet portions or panels 302, 303, as in the embodiment shown. They are preferably an extension of the outer topsheet portions or panels 302, 303.

The waste containment flaps 501, 502 may be treated with a suitable surfactant to modify their hydrophobicity/hydrophilicity as desired. Alternatively, the waste containment flaps 501, 502 may be formed as separate elements and then attached to the body side liner. In this alternative embodiment, the central topsheet portion or panel 301 may extend past the connection point with the waste containment flaps 501, 502, and even extend to the periphery of the backsheet. Still further, the central topsheet portion or panel 301 could extend fully between the outer topsheet portions or panels 302, 303 and the sublayer 344 and even beyond so that the outer edges 305 of the central topsheet portion or panel 301 are coextensive with and sandwiched between the outer topsheet portions or panels 302, 303 and the backsheet 32.

The waste containment flaps 501, 502 preferably include a portion 503 which folds over onto itself to form a small enclosure. At least one, and depending on the size of the enclosure sometimes more than one, elastic member 504 (FIG. 2) is secured in the enclosure in a stretched condition. As has been known at least as long the disclosure of Tetsujiro, Japanese Patent document 40-11543, when the flap elastic 504 attempts to assume the relaxed, unstretched condition, the waste containment flaps 501, 502 rise above the surface of the central topsheet portion or panel 301.

The waist elastics 38a, 38b may be similar structures or different to impart similar or different elastic characteristics to the front and back waist portions of the diaper. In general, the waist elastics may comprise foam strips positioned at the front and back waist sections 22, 24. The foam strips are preferably about ½ to 1½ inches wide and about 3–6 inches long. The foam strips are preferably positioned between the top sheet portions or panels and the back sheet 32. Alternatively, a plurality of elastic strands may be employed as waist elastics rather than foam strips. The foam strips are preferably polyurethane, but could be any other suitable material which decreases waist band roll over, reduces leakage over the waist ends of the absorbent garment, and generally improve comfort and fit. The front and back waist foam strips 38a, 38b are stretched 50–150%, preferably 100% before being adhesively secured between the back sheet 32 and top sheet 30.

In any or all of the foregoing embodiments, the top sheet may comprise a single sheet of material having different characteristics (e.g., liquid-imperviousness/perviousness and/or hydrophobicity/hydrophilicity) and have regions of transition or demarcation therebetween.

Each leg opening 28a, 28b is provided with a leg elastic containment system 36. In the preferred embodiment, three strands of elastic threads are positioned to extend adjacent to leg openings 28a, 28b between the outer top sheet portions or panels 302, 303 and the back sheet 32. Any suitable elastomeric material exhibiting at least an elongation (defined herein as $L_S-L_R/L_R$ where Ls is the stretch length of an elastic element and $L_R$ is retracted length, multiplied by 100 to obtain percent elongation) in the range of 5%–350%, preferably in the range of 200%–300%, can be employed for the leg elastics 36. The leg elastics 36 may be attached to the diaper 10 in any of several ways which are known in the art. For example, the leg elastics 36 may be ultrasonically bonded, heat/pressure sealed using a variety of bonding patterns, or glued to the diaper 10.

Various commercially available materials can be used for the leg elastics 36, such as natural rubber, butyl rubber or other synthetic rubber, urethane, elastomeric materials such as LYCRA (DuPont), GLOSPAN (Globe) or SYSTEM 7000 (Fulflex).

The fastening system 40 of the preferred embodiment is attached to the back waist region 24, and preferably comprises tape tab or mechanical fasteners 401. However, any fastening known in the art will be acceptable. Moreover, the fastening system 40 may include a reinforcement patch below the front waist portion so that the diaper may be checked for soiling without compromising the ability to reuse the fastener. Alternatively, other diaper fastening systems are also possible, including safety pins, buttons, and snaps.

As stated previously, the invention has been described in connection with a diaper. The invention, however, is not intended to be limited to application only in diapers. Specifically, the absorbent laminates of the preferred embodiments may be readily adapted for use in other absorbent garments besides diapers, including, but not limited to, training pants, feminine hygiene products and adult incontinence products.

The underlying structure beneath the topsheet 30 may include, depending on the diaper construction, various combinations of elements, but in each embodiment, it is contemplated that the absorbent garment will preferably include an absorbent core comprising one or more laminates positioned between the topsheet 30 and backsheet 32. The absorbent core may take a number of different constructions, depending on how the laminates are configured with respect to one another. However, in each, one of the laminates has a layer preferably containing about 50–95% by weight SAP.

Figure 3:
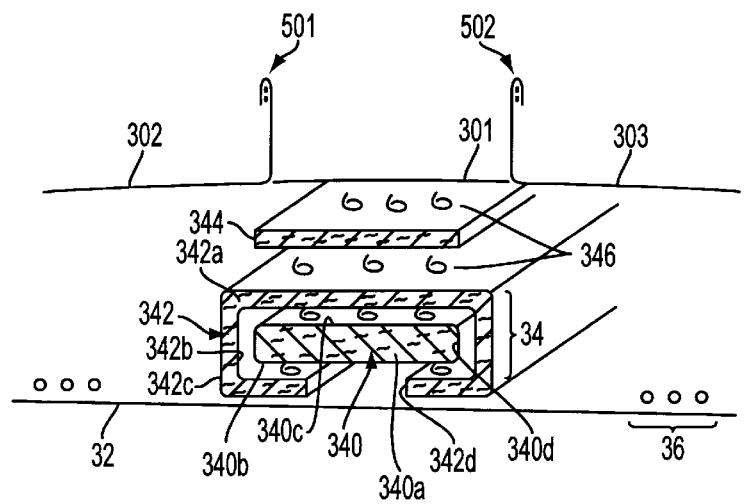
FIG. 3 is an exploded partial cross-sectional schematic perspective view of the absorbent garment of FIG. 2.
Figure 8:
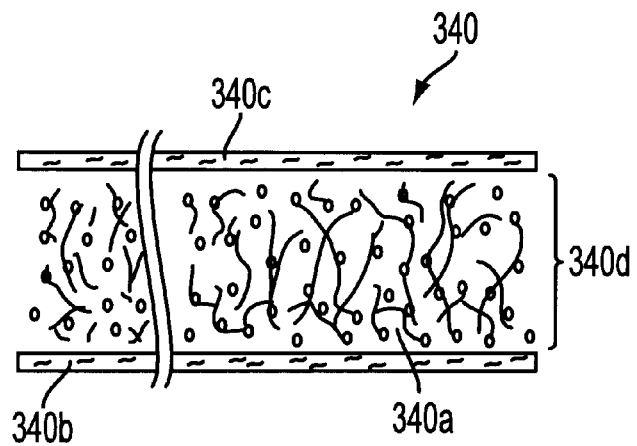
FIG. 8 is a cross-section of one of the laminates in the absorbent core of the preferred embodiments.

With particular reference to FIG. 3, there is illustrated an exploded partial cross-sectional schematic view of the absorbent core 34 according to one preferred embodiment of the invention. The absorbent laminate 34 comprises a central absorbent laminate 340 and a wrapping absorbent laminate 342 enveloping the central laminate 340. With particular reference to FIG. 8 in conjunction with FIG. 3, the construction of central laminate 340 is depicted. Central laminate 340 comprises a central absorbing layer 340a sandwiched between upper and lower tissue layers 340b, 340c. The upper and lower tissue layers 340b, 340c are preferably substantially co-terminous with the upper and lower surfaces of the central absorbing layer 340a or alternatively layers 340b, 340c may be slightly wider than the upper and lower surfaces of central absorbing layer 340a.

The construction of absorbent laminate 342 is preferably substantially the same as the construction of absorbent laminate 340 insofar as both laminates 340, 342 preferably comprise three layers: a central absorbing layer sandwiched between tissue layers. More particularly, wrapping laminate 342 comprises an absorbing layer 342a sandwiched between an inner tissue layer 342b and an outer tissue layer 342c. Once again, the end edges 342d of wrapping laminate 342 remain substantially exposed without being covered by tissue layer 342b, 342c. Under normal circumstances, having exposed side edges of an absorbent laminate comprising about 50–95% by weight SAP may be problematic in that SAP may tend to readily escape from the side edges. The escape or leakage of SAP from the side edges 340d, 342d of absorbent laminate 340 and wrapping laminate 342 is attenuated by the fact that absorbent laminate 340 is substantially encased within wrapping laminate 342, particularly along the exposed side edges 340d thereof. Likewise, the leakage of SAP along exposed side edges 342d of wrapping laminate 340 is attenuated by the fact that the bottom of absorbent laminate 340 substantially captures and retains any migrating SAP between bottom tissue layer 340b and backsheet 32.

Optionally, an upper or transfer layer 344 may be positioned on top of the wrapping laminate 342. The transfer layer 344 is technically not part of the absorbent core 34, but rather facilitates the transfer of liquid to the absorbent core 34. Each of the layers are laminates and preferably attached to one another by spray adhesive or thermal bonding 346. The central laminate 340 and wrapping laminate 342 are preferably rectangular in length, i.e., the fiber laminate absorbent core does not extend into the ears 302, 303 (FIG. 1) of the absorbent garment, but could be readily modified to do so.

In order to conserve materials, but without materially sacrificing performance, the absorbent core of FIG. 3 may be configured so that central laminate 340 extends along only a fraction of the length of the absorbent garment. For example, if the wrapping laminate 342 extends the entire length of the garment, central laminate 340 may be positioned only on substantially the front half of the garment. The basis weight of the partial-length central laminate 340 is preferably greater than that of the full-length wrapping laminate 342. The basis weight of the partial-length central laminate 340 is about 200–400 gsm, preferably about 300 gsm. The basis weight of the full-length wrapping laminate 342 is about 100–200 gsm, preferably about 150 gsm. The composition of each laminate can be modified independently for optimal core performance. For example, in some absorbent core designs, one of the laminates of the absorbent core 34 may function as an acquisition/distribution layer, whereas in others as a storage layer.

Figure 4:
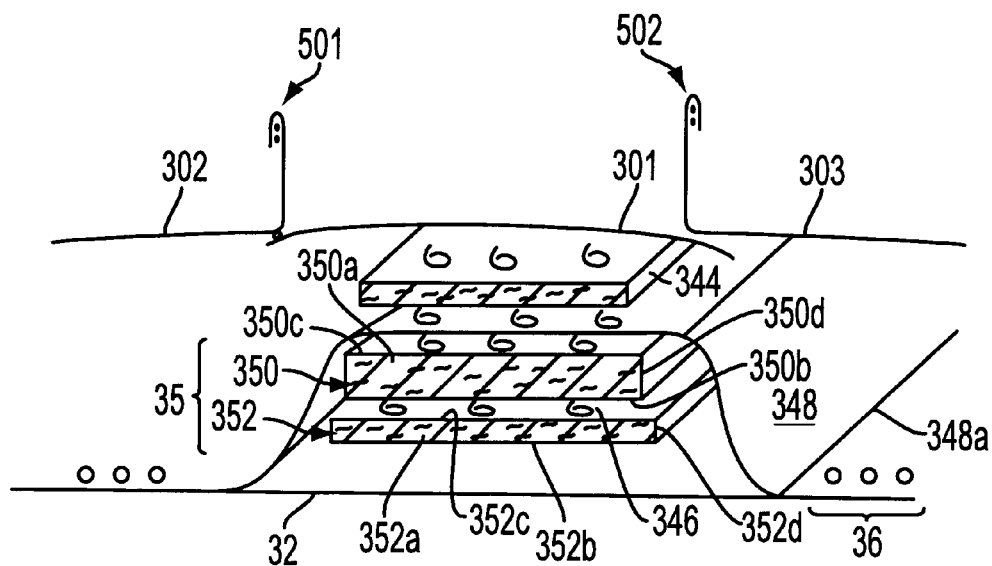
FIG. 4 is an exploded partial cross-sectional schematic perspective view, similar to FIG. 3, but illustrating another preferred embodiment for the fiber laminate absorbent core.

Another preferred absorbent core construction is depicted as an exploded partial cross-sectional schematic view in FIG. 4. There, the absorbent core 35 comprises an upper laminate 350 and a lower laminate 352.

Upper laminate 350 comprises a central absorbing layer 350a sandwiched between tissue layers 350b, 350c. Tissue layers 350b, 350c are substantially co-terminous with the lower and upper surfaces, respectively, of central absorbing layer 350a. The side edges 350d of central absorbing layer 350a are substantially uncovered by either of tissue layers 350b, 350c. Similarly, lower laminate 352 comprises a central absorbing layer 352a sandwiched between tissue layers 352b, 352c. Tissue layers 352b, 352c are substantially co-terminous with the lower and upper surfaces of central absorbing layer 352a. The side edges 352d of central absorbing layer 352a remain substantially uncovered by tissue layers 352b, 352c. At least one, and preferably both, of central absorbing layers 350a, 352a comprise at least about 50–95% SAP by weight. Again, the fact that side edges 350d, 352d of central absorbing layers 350a, 352a are substantially uncovered by tissue layers would normally be problematic since, due to the high concentration of SAP, the SAP would tend to migrate out the side edges 350d, 352d and not be positioned in use for optimum distribution and containment of urine. In order to ensure that the SAP is contained within the side edges 350d, 352d of central absorbent layers 350a, 352a, a tissue layer 348 is positioned above tissue layer 350c and extends around the side edges 350d, 352d of upper and lower laminates 350, 352. The side edges 348a of tissue layer may be bonded to backsheet 32 between the laminate 35 and leg elastics 36 or alternatively may wrap beneath laminate 35. Consequently, the lateral migration of SAP out the side edges 350d, 352d is substantially prevented.

It will be appreciated that a variety of optional tissue transfer and acquisition layers may be included within the absorbent garment between topsheet 30 and backsheet 32. The absorbent core 35 of the embodiment of FIG. 4, however, comprises at least one and preferably two absorbent laminates 350, 352, at least one of which and preferably both of which have central absorbing layers 350a, 352a having at least about 50–95% by weight SAP.

Transfer or acquisition layer 344 may optionally be positioned between tissue layer 348 and central topsheet panel 301. Each of the laminates and tissue, acquisition or transfer layers are preferably thermally bonded or adhesively bonded to adjacent layers as indicated by adhesive bonds 346. Hot melt adhesive is preferably applied to the outer surfaces of the tissue layer of laminates and optionally to the surfaces of any tissue, acquisition or distribution layers.

Other equivalent laminate configurations are within the purview of the preferred embodiments, so long as one of the absorbent laminates, e.g., layers 340, 342, 350, 352 in FIGS. 3 and 4, comprises at least about 50–95% by weight SAP.

Like the embodiment of FIG. 3, the upper laminate 350 of the embodiment of FIG. 4 may be designed to extend along only a fraction of the length of the absorbent garment. In addition, as above, the absorbent core 35 of FIG. 4 is preferably rectangular in shape and generally does not extend into the ears 302, 303 of the absorbent garment, but could be modified to do so. Another laminate configuration reverses the positioning of the upper and lower layers 350, 352 so that laminate 352 is on top of laminate 350.

One layer of the absorbent laminate of the alternative embodiment is preferably placed on or beneath a traditional fluff or fibrous absorbent core. The absorbent laminate of the preferred embodiments is particularly ideal for narrow crotch diapers and training pants. Narrow crotch training pants either must typically sacrifice absorbent capacity at the narrowed portion as a result of reduced absorbent surface area, or must alternatively provide a thicker absorbent core to compensate for the reduced surface area. As the thickness of the core increases, comfort, fit and wearability decrease. By using the high absorbency absorbent laminate of the preferred embodiments in a narrow crotch absorbent garment, the absorbent capacity through the central crotch area is not sacrificed while comfort fit and wearability are improved.

Traditional hourglass shaped absorbent cores have pulp/SAP regions extending through the front and rear portions thereof. The ear regions of the absorbent garment thus compensate for the narrow, rectangularly shaped absorbent laminate of the preferred embodiments which does not extend into the ears of the diaper. This alternative absorbent core design with a narrow crotch can be thought of as a "mixed core." It combines the advantageous features of the absorbent laminate of the preferred embodiments with the traditional fluff/SAP absorbent cores.

Figures 9A, 9B, 9C:
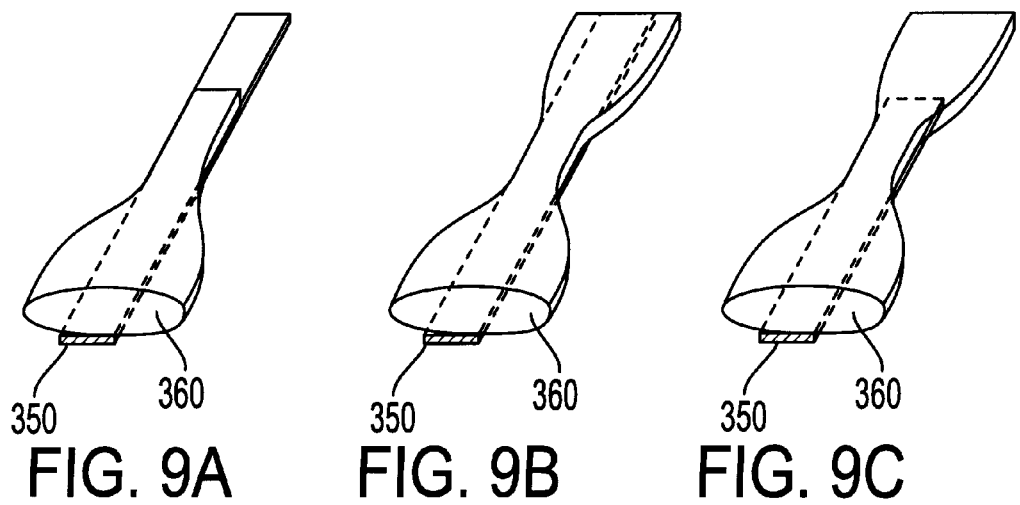
FIGS. 9A–9C are schematic perspective views of alternative absorbent core embodiments.

For example, as shown in FIGS. 9A–9C, the absorbent core may comprise a variety of alternative embodiments including narrowed crotch regions forming T-shaped or hourglass-shaped cores. More specifically, in the embodiment of FIG. 9A, the absorbent core 35 comprises one or more rectangularly shaped or C-folded laminates having a high SAP concentration as described above and extending substantially from the front waist region to the rear waist region of the absorbent garment. A T-shaped conventional pulp/SAP partial length absorbent layer may be positioned above absorbent laminate 350 to improve urine acquisition and containment throughout the front half of the absorbent article.

As shown in FIG. 9B, the absorbent core 35 may comprise a full length rectangularly shaped absorbent laminate 350 containing 50–95% by weight SAP. The absorbent core 35 further may include a full length hourglass-shaped conventional pulp/SAP layer positioned above absorbent laminate 350. In the crotch region, the conventional pulp/SAP absorbent layer is narrowed for improved comfort and fit. Finally, as shown in FIG. 9C, the absorbent core 35, according to the preferred embodiments, may include a partial length absorbent laminate 350 containing about 50–95% by weight SAP. A full length hourglass-shaped conventional pulp/SAP layer may be positioned above absorbent laminate. In the crotch region, the conventional pulp/SAP layer is narrowed in the crotch region for improved comfort and fit. Although only one absorbent laminate is depicted in FIGS. 9A–9C, additional absorbent laminates, each of which contains a central absorbing layer of 50–95% by weight SAP may be positioned below absorbent laminate 350 or above the conventional pulp/SAP absorbent layer. Absorbent laminates used in narrow crotch absorbent cores preferably have a total basis weight in the range of 300–600 g/sm.

Tissue, airlaid fluff pulp, and synthetic nonwoven are preferred materials for layer 344 of FIGS. 3 and 4. Layer 344 acts as a transfer layer to rapidly spread and transport urine to the surface of the absorbent core 34, 35. Tissue basis weights of about 10–40 grams per square meter, airlaid pulp basis weights of about 30–120 grams per square meter, and synthetic nonwoven basis weights of about 10–150 grams per square meter are preferred for transfer layer 344.

In an alternative configuration, each of the absorbent laminates 340, 342, 350, 352 may optionally be constructed using different combinations of materials for the upper 340c, 342c, 350c, 352c and lower 340b, 342b, 350b, 352b layers. For example, laminate 340 may comprise airlaid fluff pulp or synthetic nonwoven for the upper layer 340c and tissue for the lower layer 340b. Basis weights similar to those above would be preferred for the upper and lower layers of laminates 340, 342, 350, 352.

The present invention is premised in part on the unexpected discovery that certain fibrous and particulate additives as constituent elements of an absorbent core laminate maintain high SAP efficiencies when the SAP concentration is in the range of about 50–95% and more preferably about 60–90% and most preferably about 75–85%. Super absorbent polymers of the surface cross-linked variety perform best in these laminates. These additives are preferably constituent elements of the central absorbing layers 340a, 342a, 350a, 352a. Fibrous additives of central absorbing layers 340a, 342a, 350a, 352a preferably include, but are not limited to, cellulose acetate fibers, rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, or blends thereof. Of the foregoing, cellulose acetate is the most preferred fibrous additive. In addition, rayon, Courtauld's LYOCELL, polyacrylonitrile, cotton fibers and cotton linters have similar properties to cellulose acetate and are alternatively preferred. The remaining fibers, surface-modified polyolefin/polyester bicomponent fibers, and surface-modified polyester/polyester bicomponent fibers are also believed to be effective fibrous additives. To maintain high SAP concentrations, the concentration of fibrous additives in the central layer 340 of the laminate is preferably about 5–50% and more preferably about 10–30% and most preferably about 15–25%. Most preferably, the central layer 340 comprises about 75–85% SAP and 15–25% fibrous additives selected from the foregoing group.

It has further been unexpectedly discovered that particulate additives may be added to central layer 340 in addition to or as a substitute for the foregoing fibrous additives in order to maintain high SAP efficiency. The particulate additives are preferably insoluble, hydrophilic polymers with particle diameters of 100 μm or less. The particulate additives are chosen to impart optimal separation of the SAP particles. Examples of preferred particulate additive materials include, but are not limited to, potato, corn, wheat, and rice starches. Partially cooked or chemically modified (i.e., modifying hydrophobicity. hydrophilicity, softness, and hardness) starches can also be effective. Most preferably, the particulate additives comprise partially cooked corn or wheat starch because in this state, the corn or wheat are rendered larger than uncooked starch and even in the cooked state remain harder than even swollen SAP. In any event, regardless of the particulate additive chosen, one of the important criteria and objectives is to use particulate additives which are hard hydrophilic materials relative to swollen SAP or which are organic or inorganic polymeric materials about 100 microns in diameter. Fibrous and particulate additives can be used together in these absorbent laminates. Some examples of SAP/particulate and SAP/fiber/particulate additives may include:

| | % Basis Weight | | | | |
|---|---|---|---|---|---|
| Material | Example A | Example B | Example C | Example D | Example E |
| SAP | 95% | 90% | 85% | 80% | 75% |
| Fiber | 0% | 0% | 15% | 15% | 15% |
| Particulate | 5% | 10% | 0 | 5% | 10% |

Total basis weights of the central laminate 340 including SAP, tissue and additives, are about 200–400 grams per square meter. The most preferred total basis weights of the central laminate 340 are about 250–350 grams per square meter. Similar basis weights are preferred for laminate 350. Total basis weights of laminates 342, 352 are 50–300 gsm and most preferably 100–200 gsm. The foregoing fibrous additives maintain high SAP efficiency at high SAP concentrations even when they are mixed with soft or hard wood fluff pulp fibers. For example, it has been unexpectedly discovered that the SAP efficiency improves to about 85% in a 150 grams per square meter composite comprised of 80% SAP, 10% cellulose acetate, and 10% fluff pulp whereas in a composite comprised of 80% SAP and 20% fluff pulp SAP efficiency is about 70%.

Optionally, about 1–10%, preferably about 5%, by weight of thermally bondable synthetic fibers can be added to the central laminate 340 to impart additional wet strength to the laminate. This will improve the stability of the core during use of the diaper. The preferred synthetic fibers are polyolefin/polyester fibers and polyester/polyester bicomponent fibers.

While, as discussed above, the present invention is premised in part on the unexpected discovery that certain fibrous and particulate additives maintain high SAP efficiencies when the SAP concentration is in the range of about 50–95%, fluff/SAP cores that contain greater than about 50% SAP require additional structural or design measures to contain the SAP in the core and provide adequate wet strength for core stability in manufacture and use. One solution is to adhesively or thermally bond the absorbent material to improve wet strength and core stability. This, unfortunately, results in slower than adequate rates of absorption and poor SAP efficiency. Another solution resides in the unexpected discovery that a high SAP concentration absorbent layer 340*a* (FIG. 8) may be hydrogen bonded to additional fibrous layers as illustrated in FIGS. 3, 4 and 9. When a highly concentrated SAP-containing absorbent layer 340*a* is hydrogen bonded to upper and lower layers 340*c*, 340*b* or wrapped by a fibrous layer 342 (FIG. 3), the SAP efficiency is not impaired, wet strength increases, and the upper and lower layers 340*c*, 340*b* and wrapping layer 342 add stability to the core during manufacture.

Prior art roll good SAP composites containing 50–95% SAP are often too weak for processing on a diaper machine, have inadequate wet strength for in-use core stability, and the SAP is not secured within the composite. Those roll goods that have adequate strength tend to have low SAP efficiency because they restrict swelling of the SAP in the composite. Attempts to bond the SAP within the composite invariably reduces the absorbency and efficiency of the composite. The absorbent cores 34, 35 of the preferred embodiments solves the prior art problems of maintaining adequate levels of dry tensile strength, core stability in use, and SAP containment. The structure and composition of the absorbent laminates 340, 350 are preferably designed for optimal absorbency and SAP efficiency. The structure and composition of the absorbent laminates 342, 352 are preferably designed for optimal strength, SAP containment, and liquid distribution.

Depending on whether a wet or dry process is used to make the laminates 340, 350, bonding absorbent layers 340*a*, 350*a* with tissue layers 340*b*, 340*c*, 350*b*, 350*c* can be achieved with hydrogen or adhesive bonds. If the material used to form the laminates 340, 350 contains about 1–5% by weight thermally bondable synthetic fibers, bonding can be achieved with thermal bonds. When the upper and lower layers are tissue layers and are hydrogen bonded using water to middle layer 340*a*, 350*a*. unexpectedly good "core utilization" is realized. "Core utilization" is the percentage of the total capacity of a core that can be absorbed in a demand absorbency test. This unexpected performance improvement is believed to be the result of the good liquid distribution achieved with a high density, non-gel blocking central layer 340*a*, 350*a* and using a tissue layer that is intimately bonded to the fibers of the absorbent layer 340*a*, 350*a* of the laminate.

Figure 5:
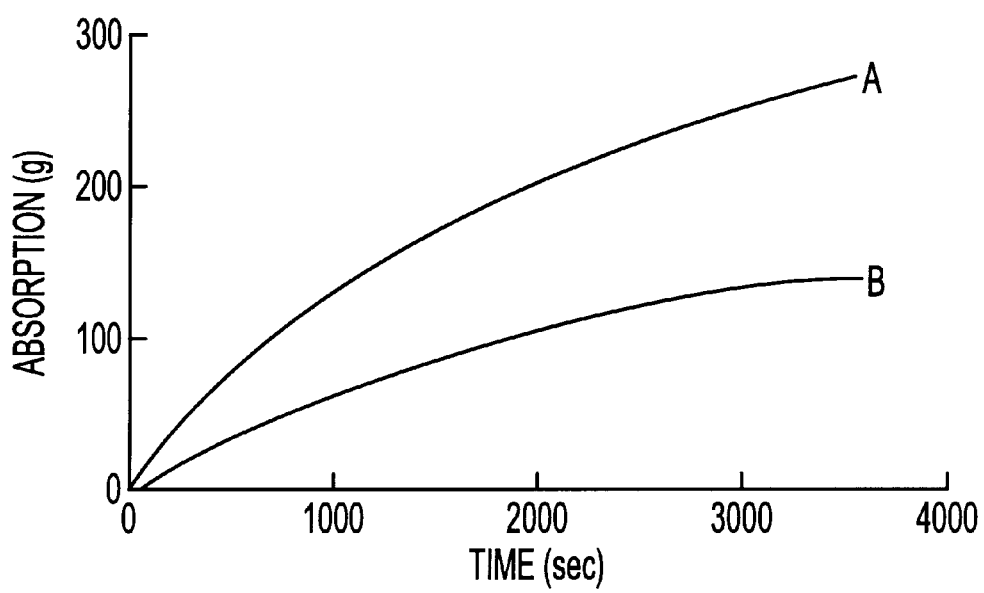
FIG. 5 is a graph of absorption vs. time for two fiber laminate absorbent cores according to the preferred embodiments.

For example, with reference to FIG. 5, the unexpectedly improved performance of utilizing the hydrogen bonded tissue to opposed faces of a high density absorbent laminate comprising 20% cellulose acetate and 80% SAP is illustrated. The graph of FIG. 5 plots demand absorbency vs. time, an important indicator of the effectiveness of absorbent garments. Demand absorbency testing describes the absorbency of the specimen which when placed on a porous surface, the fluid is drawn into the core by capillary action. The laminates of FIG. 5 both comprise wet-laid or dry formed cellulose acetate (20%)-SAP (80%), with tissue secured to the cellulose acetate SAP layer. The absorbent core represented by curve A was formed by hydrogen bonding the tissue layers of the laminate to the absorbent material and drying the laminate in a compressed state. The absorbent core represented by curve B was of comparable composition, but the tissue layers were not hydrogen bonded to the central layer. Rather, in curve B, the tissue layers were adhesively attached to the absorbent material. Hydrogen bonding of tissue to the central layer 340*a* results in a central layer of higher density. The absorbent core represented by curve A absorbed more than twice the fluid as the core of curve B in the same amount of time, indicating a large increase in core utilization when tissue layers are hydrogen bonded to a compressed cellulose acetate/SAP web.

The preferred fiber absorbent core laminates have an optimum density for SAP efficiency and core utilization. SAP efficiency decreases and core utilization increases as core density increases. Thus, a compromise is usually made. For a 200–400 grams per square meter cellulose acetate (80%)/SAP (20%) laminate, the optimum density range for the central layer 340 is preferably about 0.25–0.45 gcc, and more preferably about 0.30–0.40 gcc, and most preferably about 0.35 gcc.

Figure 6:
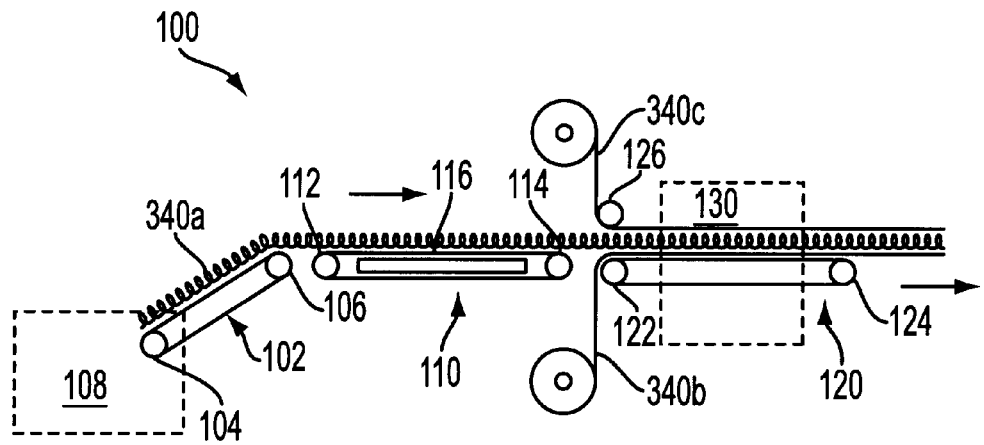
FIG. 6 is a schematic illustration of one method of manufacturing the fiber laminate absorbent core of the preferred embodiments.
Figure 7:
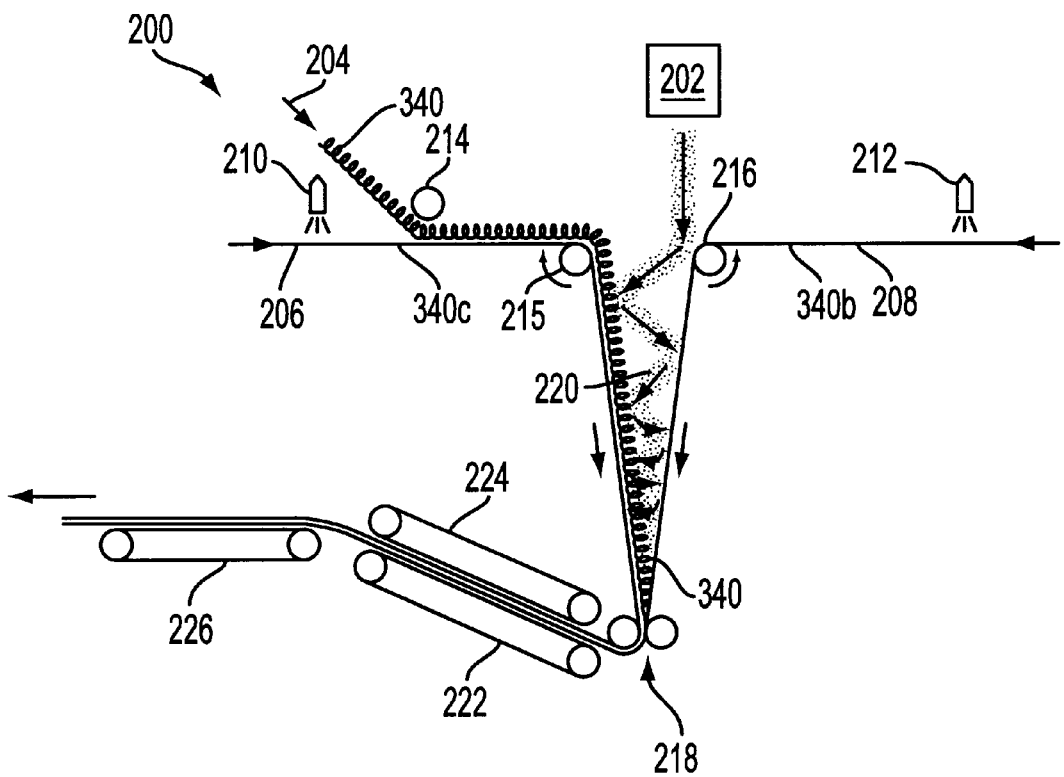
FIG. 7 is a schematic illustration of another method of manufacturing the fiber laminate absorbent core of the preferred embodiments.

The foregoing absorbent laminates of the preferred embodiments may be made using both wet and dry processes, described below. With reference to FIGS. 6–7. the manufacturing process for producing the absorbent laminates of FIG. 8 according to wet and dry processes, respectively, are schematically illustrated.

The fiber/particulate and SAP laminate 340 can be made using conventional wet processes such as, for example, conventional wet-laid nonwoven processes utilizing Valmet's high dilution Deltaformer or Rotoformer, an aqueous foam-based forming process, or a process of coating a porous substrate with a solvent/water-based suspension of the fiber/particulate and SAP. An example of one such wet process, the machinery of which is available from Neue Bruderhaus AG is schematically illustrated in FIG. 6. There, the manufacturing line 100 for forming laminate 340 comprises a first endless conveying system 102, e.g., felt or wire mesh, extending between rollers 104, 106. Conveyor 102 is inclined, with its lower end submersed within a slurry containment bath 108 of fibrous/particulate additives and SAP. Conveyor 102, depending on the angle of incline and the static friction of the felt or wire mesh, entrains a predetermined amount of slurry from bath 108. The composite is delivered to a second conveyor 110.

Second conveyor 110 likewise includes rollers 112, 114, between which extends mesh wire or felt. A suction dewatering device 116 is positioned within conveyor 110. Water is removed from the fibrous/particulate additive and SAP composite, upon which the composite is delivered to third conveyor 120. Third conveyor includes rollers 122, 124, between which extends mesh wire. Upper and lower layers 340*c*, 340*b* of absorbent laminate 340 are formed as roll goods positioned above and below third conveyor 120. Upper and lower layers 340*c*, 340*b* may comprise tissue, airlaid fluff pulp or synthetic nonwoven. Nip roller 126 presses upper layer 340*c* into intimate engagement with the upper surface of absorbent layer 340*a*. Likewise, roller 122 presses lower layer 340*b* into intimate engagement with the lower surface of absorbent layer 340*a*.

Finally, a drying oven 130 is positioned around third conveyor. Drying oven heat the fiber absorbent core laminate 34, removing excessive water, and causing the adjacent layers to intimately bond together, either by thermal bonds or hydrogen bonds. If the upper or lower layer is a synthetic nonwoven, or contains thermally bondable fibers, it can bond to the thermally bondable fibers included in the wet-laid middle layer for added wet strength. Additional bonding strength can be imparted by hot calendaring or thermal point bonding.

With reference to FIG. 7, the absorbent laminate 340 manufactured according to a dry forming process is illustrated. The dry process typically has lower conversion costs than the wet process, since the equipment used in a dry process is typically less complex and can run at higher line speeds. Further, the dry forming process could be adapted for use on individual diaper machines rather than forming the absorbent composite laminate off line and then prepared as a roll good as in the wet process. Alternatively, wet processes may be employed on or off line.

One of the challenges in a dry forming process is achieving homogeneous mixing of SAP with other components, i.e., fibrous or particulate additives, of the absorbent layer 340*a* of the laminate. With the proper geometry of the web path, substantial homogeneous mixing of SAP can be realized. The preferred dry forming machine 200 of FIG. 7 includes a SAP bin 202, a fiber feed path 204, an upper layer feed path 206 and a lower layer feed path 208. Hot melt adhesive spray applicators 210, 212 apply adhesive to the inner surfaces of upper and lower layers 340*c*, 340*b*, respectively. Hydrophilic hot melt adhesives are effective processing aids but not critical in the construction of the dry laminates if hydrogen bonding is used. A typical application level of hot melt adhesive is about 1–10 gsm per layer. Roller 214 intimately engages the fibrous additive from feed path 206 with upper layer 340*c*.

SAP is vertically dropped from SAP bin 202 to a point above roller 216. A region of high turbulence 220 is generated between the upper 340*c* and lower 340*b* layers of the laminate just before a nip point 218 that stabilizes the structure. The high turbulence or mixing chamber 220 is designed so that the angle and high speed of the moving web causes the SAP stream to be deflected downward toward the upper layer 340*c*, to which the fibrous additive component is attached. The SAP bounces back and forth between the upper and lower layers 340*c*, 340*b*, effectively and evenly distributing the SAP within the fibrous component. SAP lost at the edges of the 2 to 4 meter wide web can be collected and recycled back into the process. When the laminate 340 is compressed at nip 218, the SAP is uniformly mixed and effectively locked within the structure. As is known in the art, individual particles of SAP are preferably not bonded to the fiber component or the outer layers, but are rather preferably locked within the absorbent layer 340*a* due to the pore size of the fibrous additive.

Alternatively, the absorbent laminate may be made directly on the diaper converting machine. In such a situation, the laminate is formed using the dry process wherein tissue layers 340*c*, 340*b* are wider than the fiber/SAP layer to reduce SAP losses along the edges of the absorbent laminate. The edges 340*c*, 340*b* of the laminate are then adhesively attached to completely envelope and contain the fiber/SAP layer.

The fibrous component of the absorbent layer 340*a* is most preferably a crimped tow of cellulose acetate or polyester. Alternatively, the fibrous component of the absorbent layer 340*a* may be a low-density roll good made in a separate process. Still further yet, the fibrous component could also be a carded web formed on-line. Optionally, it is advantageous to introduce 1–5% of a thermally bondable fiber into the fibrous component of the absorbent layer 340*a* for wet strength and core stability in use.

If, for improved absorbency, hydrogen bonding is desired in the dry forming process, after the laminate is formed the upper and lower layers 340*c*, 340*b* may be lightly wetted between endless conveyors 222, 224, and then dried at a drying conveyor 226 incorporating either an IR oven or an air dryer. When making a cellulose acetate-SAP-tissue laminate, triacetin can be dispersed in the water of the wetting section corresponding to conveyors 222, 224 to provide additional bonding within the structure. When water with hydrogen bonding is used, the consumption of hot melt adhesive is typically reduced significantly.

As will be appreciated, several permutations and combinations of laminates are possible. Without intending to limit the claimed invention or equivalents thereof, some of the preferred exemplary laminates for use in an absorbent core of an absorbent garment include:

EXEMPLARY ABSORBENT CORE LAMINATES

| Example | Type of Laminate | For Use In (Type of Diaper) | Total Basis Weight (g/sm) | Absorbent Laminate Upper Layer | Absorbent Laminate Central Layer | Absorbent Laminate Lower Layer |
|---|---|---|---|---|---|---|
| 1 | Low BW Laminate | FIG. 3, 4 | 182 g/sm | Tissue 16 g/sm | 80% SAP; 20% Cellulose Acetate 150 g/sm | Tissue 16 g/sm |
| 2 | High BW Laminate | FIG. 3, 4 | 332 g/sm | Tissue 16 g/sm | 80% SAP; 20% Cellulose Acetate 300 g/sm | Tissue 16 g/sm |
| 3 | Low BW Laminate with Acquisition/Distribution Function | FIG. 3 | 206 g/sm | Latex-bonded Airlaid 40 g/sm | 80% SAP; 20% Cellulose Acetate 150 g/sm | Tissue 16 g/sm |
| 4 | Low BW Laminate with Acquisition/Distribution Function | FIG. 3 | 182 g/sm | Tissue 16 g/sm | 70% SAP; 20% Cellulose Acetate; 10% Bico 150 g/sm | Tissue 16 g/sm |
| 5 | High BW Laminate with Acquisition/Distribution Function | FIG. 4 | 356 g/sm | Latex-bonded Airlaid 40 g/sm | 80% SAP; 20% Cellulose Acetate 300 g/sm | Tissue 16 g/sm |
| 6 | High BW Laminate with Acquisition/Distribution Function | FIG. 4 | 356 g/sm | 80% Polyester; 20% Bico 40 g/sm | 80% SAP 20% Cellulose Acetate 300 g/sm | Tissue 16 g/sm |

-continued

EXEMPLARY ABSORBENT CORE LAMINATES

| Example | Type of Laminate | For Use In (Type of Diaper) | Total Basis Weight (g/sm) | Absorbent Laminate | | |
|---|---|---|---|---|---|---|
| | | | | Upper Layer | Central Layer | Lower Layer |
| 7 | High BW Laminate with Acquisition/ Distribution Function | FIG. 4 | 322 g/sm | Tissue 16 g/sm | 60% SAP; 20% Cellulose Acetate; 15% polyester; 5% BICO 300 g/sm | Tissue 16 g/sm |
| 8 | High BW Laminate with High SAP Content | FIG. 3, 4 | 370 g/sm | Tissue 35 g/sm | 90% SAP; 5% Cellulose Acetate; 5% Corn Starch 300 g/sm | Tissue 35 g/sm |
| 9 | High BW Laminate for Narrow Crotch Diapers | FIG. 9 | 482 g/sm | Tissue 16 g/sm | 85% SAP; 15% Cellulose Acetate 450 g/sm | Tissue 16 g/sm |

The absorbent laminates of Examples 1–9 realize about 90% SAP efficiency. This is a marked increase in core efficiency as compared with conventional high concentration SAP/pulp absorbent cases, which typically exhibit core efficiencies of about 70%. The following chart summarizes pulp/SAP cores of various composition. AUL defines the uptake of liquid of a specimen while a load is applied to the specimen.

| Core | AUL (g/g of SAP)* |
|---|---|
| SAP only Low BW | 30 |
| SAP only - High BW | 21 |
| 70% Pulp/30% SAP - 850 gsm | |
| Homogenous | 28 |
| Layered | 22 |
| 30% Pulp/70% SAP | 20–24 |
| Homogenous | |
| Similar to Example 2: | |
| 80% SAP/20% Cellulose Acetate at 300 gsm | 28 |

*After 30 minutes using 0.5 psi.

The invention has been described in connection with the preferred embodiments. These embodiments, however, are merely for example and the invention is not restricted thereto. It will be understood by those skilled in the art that other variations and modifications can easily be made within the scope of the invention as defined by the appended claims.

I claim:

1. An absorbent article comprising:
   a liquid permeable topsheet;
   a liquid impermeable backsheet associated with said topsheet; and
   an absorbent core positioned between the topsheet and the backsheet, the absorbent core comprising a first absorbent laminate, said first absorbent laminate comprising:
   an upper layer near the topsheet;
   a lower layer near the backsheet; and
   an absorbent layer positioned between the upper and lower layers; wherein
   the side edges of said absorbent layer are substantially uncovered by said upper and lower layers;
   said upper layer comprises a material selected from the group consisting essentially of tissue, airlaid fluff pulp and synthetic non-woven;
   said lower layer comprises material selected from the group consisting essentially of tissue, airlaid fluff pulp and synthetic non-woven; and
   said absorbent layer comprising about 50–95% SAP by weight and having a SAP efficiency (AUL) of at least 80%.

2. The absorbent article of claim 1, wherein said upper layer and said lower layer are hydrogen bonded to said absorbent layer.

3. The absorbent article of claim 1, said absorbent layer comprising fibers selected from the group consisting essentially of cellulose acetate fibers, rayon fibers, LYOCELL fibers, polyacrylonitrile fibers, cotton fibers and cotton linter fibers.

4. The absorbent article of claim 1, said absorbent layer comprising fibers selected from the group consisting essentially of surface modified (hydrophilic) polyester fibers, surface-modified polyolefin/polyester bicomponent fibers, and surface-modified polyester/polyester bicomponent fibers.

5. The absorbent article of claim 4, said absorbent layer having about 5–50% by weight concentration of fibers.

6. The absorbent article of claim 1, said first absorbent laminate having a total basis weight of about 100–400 grams per square meter.

7. The absorbent article of claim 6, said first absorbent laminate having a total basis weight of about 150–250 grams per square meter.

8. The absorbent article of claim 1, said absorbent layer further comprising up to 10% by weight fluff wood pulp fibers.

9. The absorbent article of claim 1, said absorbent layer further comprising up to 5% by weight thermally bondable fibers.

10. The absorbent article of claim 1, wherein the absorbent layer further comprises particulate additives.

11. The absorbent article of claim 10, said particulate additives comprising insoluble, hydrophilic polymers with particle diameters of 100 $\mu$m or less.

12. The absorbent article of claim 11, said particulate additives selected from the group consisting essentially of potato, corn, wheat, and rice starches, and partially cooked or modified starches.

13. The absorbent article of claim 1, said tissue, said airlaid fluff pulp and said synthetic nonwoven of said upper and lower layers having basis weights of about 10–40 grams per square meter, 30–120 grams per square meter and 10–80 grams per square meter, respectively.

14. The absorbent article of claim 1, further comprising a transfer layer positioned between said topsheet and said upper layer, said transfer layer adhesively secured to said upper layer and to said topsheet.

15. The absorbent article of claim 1, said absorbent layer further comprising particulate additives, wherein said particulate additives optimize separation of SAP particles.

16. The absorbent article of claim 15, said particulate additives comprising insoluble, hydrophilic polymers having particle diameters of about 100 μm or less.

17. The absorbent article of claim 16, said particulate additives selected from the group consisting essentially of potato, corn, wheat, and rice starches, and partially cooked or modified starches.

18. An absorbent article comprising:

a liquid permeable topsheet;

a liquid impermeable backsheet associated with said topsheet; and an absorbent core positioned between the topsheet and the backsheet, the absorbent core including:

a central absorbent laminate comprising an absorbent layer sandwiched between an upper layer and a lower layer wherein the side edges of said absorbent layer are substantially uncovered by said upper and lower layers; and a wrapping absorbent laminate substantially enclosing said central absorbent laminate;

said wrapping laminate comprises a second absorbent layer sandwiched between an outer layer and an inner layer wherein the side edges of said second absorbent layer are substantially uncovered by said outer and inner layers; and said absorbent layers of said central laminate and said wrapping laminate comprising about 50–95% SAP by weight.

19. The absorbent article of claim 18, said absorbent layers having a SAP efficiency (AUL) of at least 80%.

20. The absorbent article of claim 18, said absorbent layers being formed from fibers selected from the group consisting essentially of cellulose acetate fibers, rayon fibers, LYOCELL fibers, polyacrylonitrile fibers, surface modified (hydrophilic) polyester fibers, surface-modified polyolefin/polyester bicomponent fibers, surface-modified polyester/polyester bicomponent fibers, cotton fibers.

21. The absorbent article of claim 18, wherein the absorbent layers further comprise particulate additives.

22. The absorbent article of claim 21, said particulate additives comprising insoluble, hydrophilic polymers with particle diameters of 100 μm or less.

23. The absorbent article of claim 22, said particulate additives selected from the group consisting essentially of potato, corn, wheat, and rice starches, and partially cooked or modified starches.

24. The absorbent article of claim 18, wherein said central absorbent laminate has a length which is about half the length of said wrapping absorbent laminate.

25. An absorbent laminate for absorbent garments comprising:

a central absorbent layer formed from about 75–95% by weight superabsorbent polymer and 5–25% by weight concentration additives;

an upper layer positioned above said central absorbent layer, said upper layer selected from the group consisting essentially of airlaid fluff pulp, synthetic non-woven and tissue; and a lower layer positioned below said central absorbent layer, said lower layer selected from the group consisting essentially of airlaid fluff pulp, synthetic non-woven and tissue;

wherein the side edges of said absorbent layer are substantially uncovered by said upper and lower layers.

26. The absorbent laminate of claim 25, said additives comprising fibrous additives selected from the group consisting essentially of cellulose acetate fibers, rayon fibers, LYOCELL fibers, polyacrylonitrile fibers, surface modified (hydrophilic) polyester fibers, surface-modified polyolefin/polyester bicomponent fibers, surface-modified polyester/polyester bicomponent fibers, and cotton fibers.

27. An absorbent core for absorbent garments comprising:

an absorbent laminate comprising an absorbent layer sandwiched between an upper layer and a lower layer; wherein the side edges of said absorbent layer of said absorbent laminate are substantially uncovered by said upper and lower layers;

said absorbent layer of said absorbent laminate formed from about 75–95% by weight super absorbent polymer (SAP) and about 5–25% by weight concentration additives;

said upper and lower layers of said absorbent laminate selected from the group consisting essentially of airlaid fluff pulp, synthetic non-woven, and tissue; and an upper absorbent layer positioned above said absorbent laminate, said upper absorbent layer comprising cellulose fibers; wherein said absorbent laminate has a width dimension which is substantially constant along its length and said upper absorbent layer has varying width dimensions along the longitudinal length thereof.

28. The absorbent core of claim 27, said additives comprising fibrous additives selected from the group consisting essentially of cellulose acetate fibers, rayon fibers, LYOCELL fibers, polyacrylonitrile fibers, surface-modified (hydrophilic) polyester fibers, surface-modified polyolefin/polyester bicomponent fibers, surface-modified polyester/polyester bicomponent fibers, and cotton fibers.

29. The absorbent core of claim 27, wherein said upper absorbent layer has a length dimension which is about half that of said absorbent laminate.

30. The absorbent core of claim 27, wherein said absorbent laminate has a length dimension which is about half that of said upper absorbent layer.

31. The absorbent core of claim 27, said absorbent core adapted to be positioned in a diaper, wherein the diaper includes opposing waist regions and a narrow crotch region, said width dimension of said absorbent laminate being equal to or less than the width dimension of the crotch of the diaper.

32. The absorbent core of claim 27, said upper absorbent layer further comprising super absorbent polymer positioned adjacent to said cellulose fibers.

* * * * *